United States Patent [19]

Cooper et al.

[11] Patent Number: 5,741,757
[45] Date of Patent: Apr. 21, 1998

[54] BIOCIDAL MIXTURE OF TETRAKIS (HYDROXYMETHYL) PHOSPHONIUM SALT AND A SURFACTANT

[75] Inventors: Kenneth G. Cooper, Hagley; Robert E. Talbot, Cannock; Malcolm J. Turvey, Kidderminster, all of England

[73] Assignee: Albright & Wilson Limited, Oldbury, England

[21] Appl. No.: 407,494

[22] Filed: Mar. 17, 1995

Related U.S. Application Data

[63] Continuation of Ser. No. 264,419, Jun. 23, 1994, abandoned, which is a continuation of Ser. No. 146,457, Nov. 1, 1993, abandoned, which is a continuation of Ser. No. 42,444, Apr. 2, 1993, abandoned, which is a continuation of Ser. No. 897,608, Jun. 10, 1992, abandoned, which is a continuation of Ser. No. 663,191, Feb. 28, 1991, abandoned, which is a continuation of Ser. No. 501,374, Mar. 29, 1990, abandoned, which is a continuation of Ser. No. 893,334, Aug. 5, 1986, abandoned.

[30] Foreign Application Priority Data

| Aug. 6, 1985 | [GB] | United Kingdom | 8519677 |
| Dec. 20, 1985 | [GB] | United Kingdom | 8531372 |

[51] Int. Cl.$^6$ .............. A01N 25/30; A01N 57/10
[52] U.S. Cl. .................................................. 504/153
[58] Field of Search .................................... 504/153

[56] References Cited

U.S. PATENT DOCUMENTS

| 3,013,085 | 12/1961 | Buckler | 260/606.5 |
| 3,704,325 | 11/1972 | Stockel et al. | 260/606.5 |
| 3,821,396 | 6/1974 | Shema et al. | 504/154 |
| 3,892,845 | 7/1975 | Cunningham et al. | 424/62 |
| 3,934,004 | 1/1976 | Orren | 424/68 |
| 3,998,754 | 12/1976 | Oswald | 252/351 |
| 4,058,618 | 11/1977 | Ovchinnikov et al. | 424/273 |
| 4,091,113 | 5/1978 | Green et al. | 424/329 |
| 4,333,862 | 6/1982 | Smith et al. | 252/547 |
| 4,673,509 | 6/1987 | Davis et al. | 514/129 |

FOREIGN PATENT DOCUMENTS

| 0000694 | 2/1979 | European Pat. Off. . |
| 0105843 | 4/1983 | European Pat. Off. . |
| 0139404 | 5/1985 | European Pat. Off. . |
| 139404 | 5/1985 | European Pat. Off. . |
| 1251094 | 12/1960 | France . |
| 1251235 | 12/1960 | France . |
| 378265 | 7/1962 | Japan . |
| 2136433 | 9/1984 | United Kingdom . |
| 2145708 | 4/1985 | United Kingdom . |

OTHER PUBLICATIONS

Encyclopaedia of Chemical Technology, second edition, vol. 10 by Hirk Othmer, p. 227.

Bianucci et al, CA 80:44285, "Effect of Sodium Dodecylbenzene Sulfonate on . . . ", Ig. Mod., 65(11–12), 559–63, 1972 (Abstract).

Yamada, CA 92:70240, "Antimicrobial Action of Sodium Lavrylbenzene Sulfonate . . . ", Agric. Biol. Chem. 43(12), 2601–2, 1979.

Showa, CA 94:169448, "Emulsifier Composition for Pesticides", JP 55049041 (Dec. 10, 1980), (Abstract Only).

*Primary Examiner*—S. Mark Clardy
*Attorney, Agent, or Firm*—Frishauf, Holtz, Goodman, Langer & Chick, P.C.

[57] ABSTRACT

The biocidal activity of THP (tetrakis hydroxymethyl phosphonium) compounds is synergistically enhanced by using them in conjunction with wetting agents.

25 Claims, No Drawings

BIOCIDAL MIXTURE OF TETRAKIS (HYDROXYMETHYL) PHOSPHONIUM SALT AND A SURFACTANT

This application is a Continuation of application Ser. No. 08/264,419, filed Jun. 23, 1994 (abandoned), which is a continuation of Ser. No. 08/146,457 filed Nov. 1, 1993 (abandoned), which is a continuation of Ser. No. 08/042,444 filed Apr. 2, 1993 (abandoned), which is a continuation of Ser. No. 07/897,608 filed Jun. 10, 1992 (abandoned), which is a continuation of Ser. No. 07/663,191 filed Feb. 28, 1991 (abandoned), which is a continuation of Ser. No. 07/501,374 filed Mar. 29, 1990 (abandoned), which is a continuation of Ser. No. 06/893,334 filed Aug. 5, 1986 (abandoned).

The present invention relates to a novel biocidal mixture comprising a hydroxy alkyl phosphine compound and a surfactant. Our European Patent Application No. 84305804 describes the use as biocides of organophosphine compounds of the formula $[HORPR'n]_y X_{n-2}$, wherein n is 2 or 3 y is 1 when n is 2 or otherwise is equal to the valency of X; R is an alkylene group of 1 to 4, preferably 1, carbon atoms; each $R^1$ may be the same or different and represents an alkyl or alkenyl group having from 1 to 4 carbon atoms, or, preferably, a hydroxy alkyl group with 1 to 4 carbon atoms, and water soluble condensates of the aforesaid organophosphine compounds. In particular trishydroxymethyl phosphine and more especially the water soluble tetrakis hydroxy methyl phosphonium salts, such as tetrakis hydroxy methyl phosphonium sulphate (THPS) are preferred for use according to our aforesaid patent. However, the present invention applies to all of the claimed biocide compounds described in our aforesaid European application.

Surprisingly we have now discovered a synergism between the aforesaid organophosphine compounds and surfactants which not only improves biocidal efficacy but also facilitates biofilm penetration. A surfactant is defined as a substance which, when present at a low concentration in a system, has the property of adsorbing onto the surfaces or interfaces of the system and of altering, to a marked degree, the surface or interfacial free energies of those surfaces (or interfaces). The term "interface" indicates a boundary between any two immiscible phases; the term "surface" denotes an interface where one phase is a gas, usually air.

Our invention provides a mixture of at least one compound of the above formula with at least one anionic, non-ionic, cationic, amphoteric and/or semi-polar surfactant.

Surfactants for use in our invention typically contain hydrophobic groups such as alkenyl, cycloalkenyl, alkyl, cycloalkyl, aryl, alkyl/aryl or more complex aryl (as in petroleum sulphonates) moieties having from 8 to 22, preferably 10 to 20, typically 12 to 18 carbon atoms and a hydrophilic moiety. Other hydrophobic groups included in the invention are polysiloxane groups.

The surfactant may for example consist substantially of an at least sparingly water-soluble salt of sulphonic or mono esterified sulphuric acids, e.g. an alkylbenzene sulphonate, alkyl sulphate, alkyl ether sulphate, olefin sulphonate, alkane sulphonate, alkylphenol sulphate, alkylphenol ether sulphate, alkylethanolamide sulphate, alkylethanolamide ether sulphate, or alpha sulpho fatty acid or its esters each having at least one alkyl or alkenyl group with from 8 to 22, more usually 10 to 20, aliphatic carbon atoms.

The expression "ether" hereinbefore refers to compounds containing one or more glyceryl groups and/or an oxyalkylene or polyoxyalkylene group especially a group containing from 1 to 20 oxyethylene and/or oxypropylene groups. One or more oxybutylene groups may additionally or alternatively be present. For example, the sulphonated or sulphated surfactant may be sodium dodecyl benzene sulphonate, potassium hexadecyl benzene sulphonate, sodium dodecyl dimethyl benzene sulphonate, sodium lauryl sulphate, sodium tallow sulphate, potassium oleyl sulphate, ammonium lauryl monoethoxy sulphate, or monoethanolamine cetyl 10 mole ethoxylate sulphate.

Other anionic surfactants useful according to the present invention include alkyl sulphosuccinates, such as sodium di-2-ethyl hexylsulphosuccinate and sodium dihexylsulphosuccinate, alkyl ether sulphosuccinates, alkyl sulphosuccinamates, alkyl ether sulphosuccinamates, acyl sarcosinates, acyl taurides, isethionates, soaps such as stearates, palmitates, resinates, oleates, linoleates, and alkyl ether carboxylates. Anionic phosphate esters and alkyl phosphonates, alkyl amino and imino methylene phosphonates may also be used. In each case the anionic surfactant typically contains at least one aliphatic hydrocarbon chain having from 8 to 22, preferably 10 to 20 carbon atoms, and, in the case of ethers, one or more glyceryl and/or from 1 to 20 oxyethylene and/or oxypropylene and/or oxybutylene groups.

Preferred anionic surfactants are sodium salts. Other salts of commercial interest include those of potassium, lithium, calcium, magnesium, ammonium, monoethanolamine, diethanolamine, triethanolamine, alkyl amines containing up to seven aliphatic carbon atoms, and alkyl and/or hydroxyalkyl phosphonium.

The surfactant may optionally contain or consist of nonionic surfactants. The nonionic surfactant may be, e.g. a $C_{10-22}$ alkanolamide of a-mono or di- lower alkanolamine, such as coconut monoethanolamide. Other nonionic surfactants which may optionally be present, include tertiary acetylenic glycols, polyethoxylated alcohols, polyethoxylated mercaptans, polyethoxylated carboxylic acids, polyethoxylated amines, polyethoxylated alkylolamides, polyethoxylated alkylphenols, polyethoxylated glyceryl esters, polyethoxylated sorbitan esters, polyethoxylated phosphate esters, and the propoxylated or ethoxylated and propoxylated analogues of all the aforesaid ethoxylated nonionics, all having a $C_{8-22}$ alkyl or alkenyl group and up to 20 ethyleneoxy and/or propyleneoxy groups. Also included are polyoxypropylene/polyethylene oxide copolymers, polyoxybutylene/polyoxyethylene copolymers and polyoxybutylene/polyoxypropylene copolymers. The polyethoxy, polyoxypropylene and polyoxybutylene compounds may optionally be end-capped with, e.g. benzyl groups to reduce their foaming tendency.

Compositions of our invention may contain amphoteric surfactant.

The amphoteric surfactant may for example be a betaine, e.g. a betaine of the formula:—$R_3N^+CH_2COO^-$, wherein each R is an alkyl, cycloalkyl, alkenyl or alkaryl group and preferably at least one, and most preferably not more than one R, has an average of from 8 to 20, e.g. 10 to 18 aliphatic carbon atoms and each other R has an average of from 1 to 4 carbon atoms. Particularly preferred are the quaternary imidazoline betaines of the formula:

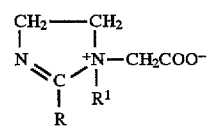

wherein R and $R^1$ are alkyl, alkenyl, cycloalkyl, alkaryl or alkanol groups having an average of from 1 to 20 aliphatic carbon atoms and R preferably has an average of from 8 to 20, e.g. 10 to 18 aliphatic carbon atoms and $R^1$ preferably has 1 to 4 carbon atoms. Other amphoteric surfactants for use according to our invention include alkyl amine ether sulphates, sulphobetaines and other quaternary amine or quaternised imidazoline sulphonic acids and their salts, and other quaternary amine or quaternised imidazoline carboxylic acids and their salts and Zwitterionic surfactants, e.g. N-alkyl taurines, carboxylated amido amines such as $RCONH(CH_2)_2N^+$ $(CH_2CH_2CH_3)_2CH_2CO_2$, and amino acids having, in each case, hydrocarbon groups capable of conferring surfactant properties (e.g. alkyl, cycloalkyl, alkenyl or alkaryl groups having from 8 to 20 aliphatic carbon atoms). Typical examples include 2 tallow alkyl, 1-tallow amido alkyl, 1 carboxymethyl imidazoline and 2 coconut alkyl N-carboxymethyl 2 (hydroxyalkyl) imidazoline. Generally speaking any water soluble amphoteric or Zwitterionic surfactant compound which comprises a hydrophobic portion including a $C_{8-20}$ alkyl or alkenyl group and a hydrophilic portion containing an amine or quaternary ammonium group and a carboxylate, sulphate or sulphonic acid group may be used in our invention.

Compositions of our invention may also include cationic surfactants.

The cationic surfactant may for example be an alkylammonium salt having a total of at least 8, usually 10 to 30, e.g. 12 to 24 aliphatic carbon atoms, especially a tri or tetra-alkylammonium salt. Typically alkylammonium surfactants for use according to our invention have one or at most two relatively long aliphatic chains per molecule (e.g. chains having an average of 8 to 20 carbon atoms each, usually 12 to 18 carbon atoms) and two or three relatively short chain alkyl groups having 1 to 4 carbon atoms each, e.g. methyl or ethyl groups, preferably methyl groups. Typical examples include dodecyl trimethyl ammonium salts. Benzalkonium salts having one 8 to 20 C alkyl group two 1 to 4 carbon alkyl groups and a benzyl group are also useful.

Another class of cationic surfactants useful according to our invention are N-alkyl pyridinium salts wherein the alkyl group has an average of from 8 to 22, preferably 10 to 20 carbon atoms. Other similarly alkylated heterocyclic salts, such as N-alkyl isoquinolinium salts, may also be used.

Alkylaryl dialkylammonium salts, having an average of from 10 to 30 aliphatic carbon atoms are useful, e.g. those in which the alkylaryl group is an alkyl benzene group having an average of from 8 to 22, preferably 10 to 20 aliphatic carbon atoms and the other two alkyl groups usually have from 1 to 4 carbon atoms, e.g. methyl groups.

Other classes of cationic surfactant which are of use in our invention include alkyl imidazoline or quaternised imidazoline salts having at least one alkyl group in the molecule with an average of from 8 to 22 preferably 10 to 20 carbon atoms. Typical examples include alkyl methyl hydroxyethyl imidazolinium salts, alkyl benzyl hydroxyethyl imidazolinium salts, and 2 alkyl-1-alkylamidoethyl imidazoline salts.

Another class of cationic surfactant for use according to our invention comprises the amido amines such as those formed by reacting a fatty acid having 8 to 22 carbon atoms or an ester, glyceride or similar amide forming derivative thereof, with a di or polyamine, such as, for example, ethylene diamine or diethylene triamine, in such a proportion as to leave at least one free amine group. Quaternised amido amines may similarly be employed.

Alkyl phosphonium and hydroxyalkyl phosphonium salts having one $C_{8-20}$ alkyl groups and three $C_{1-4}$ alkyl or hydroxyalkyl groups may also be used as cationic surfactants in our invention.

Typically the cationic surfactant may be any water soluble compound having a positively ionised group, usually comprising a nitrogen atom, and either one or two alkyl groups each having an average of from 8 to 22 carbon atoms.

The anionic portion of the cationic surfactant may be any anion which confers water solubility, such as formate, acetate, lactate, tartrate, citrate, chloride, nitrate, sulphate or an alkylsulphate ion having up to 4 carbon atoms such as a methosulphate. It is preferably not a surface active anion such as a higher alkyl sulphate or organic sulphonate.

Polyfluorinated anionic, nonionic or cationic surfactants may also be useful in the compositions of our invention. Examples of such surfactants are polyfluorinated alkyl sulphates and polyfluorinated quaternary ammonium compounds.

Compositions of our invention may contain a semi-polar surfactant, such as an amine oxide, e.g. an amine oxide containing one or two (preferably one) $C_{8-22}$ alkyl group, the remaining substituent or substituents being preferably lower alkyl groups, e.g. $C_{1-4}$ alkyl groups or benzyl groups.

Particularly preferred for use according to our invention are surfactants which are effective as wetting agents, typically such surfactants are effective at lowering the surface tension between water and a hydrophobic solid surface. We prefer surfactants which do not stabilise foams to a substantial extent.

Mixtures of two or more of the foregoing surfactants may be used. In particular mixtures of non-ionic surfactants with cationic and/or amphoteric and/or semi polar surfactants or with anionic surfactants may be used. Typically we avoid mixtures of anionic and cationic surfactants, which are often less mutually compatible.

Preferably the hydroxyalkyl phosphine compound and the surfactant are present in a relative weight concentration of from 1:1000 to 1000:1, more usually 1:50 to 200:1, typically 1:20 to 100:1, most preferably 1:10 to 50:1, e.g. 1:1 to 20:1 especially 2:1 to 15:1.

Effective doses of the mixture are typically from 2 ppm to 2000 ppm more usually 20 ppm to 1,000 ppm e.g. 50 ppm to 500 ppm especially 100 to 250 ppm.

The composition may additionally contain other biocides, water, dispersants, antifoams, solvents, scale inhibitors, corrosion inhibitors, oxygen scavengers and/or flocculants.

Our invention includes aqueous solutions containing a biocidally active concentration of a composition of the invention. Such solutions may be water systems or aqueous based products containing functional ingredients as described in our aforesaid European Patent Application. Our invention also includes anhydrous, and concentrated aqueous, formulations adapted to provide the aforesaid products on dilution with water.

Scale or corrosion inhibitors which may be added to the water to be treated in conjunction with the present invention include phosphonates, polymaleates, polyacrylates, polymethacrylates, polyphosphates, phosphate esters, soluble zinc salts, nitrite, sulphite, benzoate, tannin, ligninsulphonates, benzotriazoles and mercaptobenzothiazoles all added in conventional amounts. The scale and/or corrosion inhibitors may be added to the water separately from or in association with the phosphonium compound and surfactant. There may be added to the water to be treated oxygen scavengers, flocculants such as polyacrylamide dispersants, antifoams such as silicones or polyethyleneoxylated antifoams or other biocides such as tin compounds or isothiazolones.

The anion X of the organophosphonium salt may be chloride sulphate or phosphate. Nitrates are possible but may prove unstable. Other anions that may be present as the component X in conjunction with the organophosphonium cation include organic anions that form water soluble THP salts, such as formate, acetate, citrate, tartrate and lactate, halides such as fluoride, bromide, and iodide, bisulphite, borate, silicate, phosphonates such aceto di phosphonate and amino tris methylene phosphonate, polyphosphates such pyrophosphate, tripolyphosphate and tetraphosphate, phosphite, and hypophosphite. It is also possible to combine the THP cation and the surfactant by forming the THP salt of an anionic surfactant acid e.g. a tetrakis(hydroxymethyl) phosphonium $C_{12-14}$ linear alkyl benzene sulphonate or an alkyl sulphate, alkyl ether sulphate or alkyl sulphosuccinate.

The present invention also provides for a composition for treating water containing aquatic microorganisms which comprises an organophosphine compound as aforesaid and a surfactant, together with one or more other biocides and/or scale or corrosion inhibitors, oxygen scavengers, flocculants, dispersants and/or antifoams.

The mixture according to our invention may be prepared in situ by adding the organophosphine compound and the surfactant separately to the water system to be treated. Alternatively and preferably the components may be premixed, either alone, provided that they are miscible in the desired proportions, or with water or other solvents including $C_{1-4}$ monohydric and polyhydric alcohols or ketones, dispersants such as polyelectrolytes or solubilizers such as hydrotopes, e.g. sodium toluene sulphonate or sodium xylene sulphonate, sufficient to ensure a stable homogeneous mixture. Typically trishydroxymethyl phosphonium salts are miscible with cationic surfactants of the quaternary ammonium and phosphonium type, but mixtures with non-ionic surfactants many require dilution with water or solvents.

The microorganisms to be treated are usually bacteria, fungi, yeasts, and algae that grow in aquatic environments. Included in this classification are sulphate reducing bacteria, e.g. Desulphovibrio, which may occur in oil installations, iron bacteria, e.g. Gallionella and slime forming bacteria, e.g. Pseudomonas, which last are particularly troublesome in aerated aqueous systems.

A microorganism which causes particular concern in cooling water or in air conditioning systems is *Legionella Pneumophila*, which is responsible for Legionaires Disease. When this occurs in systems contaminated with bacterial slime conventional biocides used in water treatment are relatively ineffective against Legionella. THP salts used alone in conventional amounts also have a reduced effectiveness under these conditions. We have found that mixtures of THP salts and surfactant have a substantially enhanced biocidal effect against Legionella and other microorganism in the treatment of such systems.

The water to be treated may be industrial cooling water, e.g. for power stations or chemical plants or for steel or paper or brewing and may be used in closed circuit or in open circuit involving evaporation in cooling towers. Alternatively the water may be process water, especially process water containing significant sources of nutrients for microorganisms such as process water for paper making plants and breweries. Injection water or drilling fluids for oil fields or water produced from oil fields or water used in reverse osmosis plants, e.g. to provide industrial processes or boiler feed water, may be treated.

Other aquatic environments which may be treated with the hydroxy-alkyl phosphorus compounds and surfactants according to the method for the invention are cooling or process water in board mills, fertilizer manufacture, oil refineries, primary metals manufacture, e.g. steel or copper, petrochemicals, rubber manufacture, textile and fabric industries, industrial gas manufacture, minerals recovery, glass and ceramic manufacture, food industry, leather manufacture, heavy and light engineering, including metal fabrication and automotive engineering, furniture manufacture, electronics industry and surface coatings and adhesives manufacture and other manufacturing industries.

The process is also applicable to the treatment of geothermal water, water in domestic, industrial and institutional central heating and air conditioning systems and water used for hydrostatic testing of pipelines and vessels, swimming baths and as cooling water for ships and marine engines.

The invention is also applicable to the control of microbial contamination in a wide variety of aqueous based products. For example the aforesaid organophosphine compounds and surfactants may be added to a variety of solutions and emulsion compositions such as paints, cutting oils, bitumen and tar emulsions, adhesives, weedkillers and insecticides, as well as to solid or concentrated compositions for addition to water in the preparation of such products. The invention, therefore, further provides aqueous based products which are subject to microbial spoilage to which has been added a bacteriostatic or bactericidal quantity of an organophosphine compound as aforesaid plus surfactant. Typically such compositions consist of aqueous solutions, suspensions or emulsions of at least one functional ingredient, together with a minor proportion of a phosphorus compound plus surfactant of the invention, sufficient to inhibit growth of microorganisms therein.

The systems to which the invention is particularly applicable are those involving the circulation or storage of substantial quantities of water under conditions favouring the multiplication of bacteria, especially hardy bacteria such as *P Aeruginosa*, e.g. conditions involving maintaining or periodically raising the water to super ambient temperatures favouring bacterial proliferation, or maintaining nutrients for the bacteria in the water systems.

The invention is illustrated by the following examples:

EXAMPLE 1

A formulation was made by blending together 1 part by weight of "EMPIGEN"® BAC ("EMPIGEN" is a Registered Trademark of Albright & Wilson Limited; BAC is a 50% aqueous solution of alkylbenzylammonium chlorides) with 2 parts by weight of THPS-75 (a 75% aqueous solution of tetrakishydroxymethylphosphonium sulphate). This was formulation 1. The performance of formulation 1 as a biocide was compared to that of the THPS-75 solution in the following test:

Biocide Test

Mixed population biofilms were built up by exposing 1 cm diameter mild steel studs to a circulating seawater based medium which contained sulphate reducing bacteria and also a mixed bioflora which included aerobic and anaerobic bacteria. Over a period of 2 weeks a stable biofilm was built up on the studs and they were then extracted for use in the biocide test.

The biofilm coated studs were placed in beakers and solutions of the appropriate biocide, made up in seawater, were added and left in contact with the studs for 6 hours. At the end of this period, test were performed to measure the number of sulphate reducing bacteria on each stud. A control experiment was also carried out where no biocide was added to the seawater.

Results

| Biocide Concentration | Sulphate Reducing Bacteria per Stud | |
| --- | --- | --- |
| (ppm of formulated solution) | THPS - 75 alone | Formulation 1 |
| 0 | $10^4$ | $10^4$ |
| 250 | $10^4$ | 0 |
| 500 | $10^2$ | 0 |

The surfactant alone has been found substantially less biocidally active than THPS.

EXAMPLE 2

Plant Trial 1

A full scale trial was carried out on an industrial open evaporative cooling system with the following parameters.

(a) System Capacity : 5,000 gallons
(b) Recirculation Rate : 500 gallons
(c) Cooling Towers : Marley Double Flow
(d) Temperature drop : 5° C.

The cooling system was in continuous use and immediately prior to the trial the level of planktonic (i.e. free swimming) bacteria was $10^6$/ml. There was a 2 inch thickness of bacterial slime in the distribution trays on the cooling tower with many of the distribution holes blocked by bacterial slime.

The system was shot dosed with THPS-75 to give a level in the system water of 150 ppm. After 4 hours, the level of planktonic bacteria in the system water was less than $10^3$/ml representing a kill rate of greater than 99%. However, there was little, if any, impact on the bacterial slime and 24 hours later the water had been reinfected by the slime to give a bacterial level of $10^6$/ml.

3 weeks later a second shot dose was carried out, this time using the same level of THPS-75 (i.e. 150 ppm) but also adding 75 ppm of "EMPIGEN"® BAC. This time, in addition to killing the planktonic bacteria, the slime layer broke up and became dispersed into the system water. One week later the system was re-examined and it was found that the cooling tower distribution channels were substantially clean (i.e. at least 80–90% removal of slime had occurred).

EXAMPLE 3

Plant Trials 2 and 3

Two further plant trials were carried out and these also demonstrated the improvement in performance obtained when THPS was used in combination with surfactant. The details are as follows:

Pant Trial 2

This plant was an open evaporative cooling system with the following parameters:

(a) System Capacity : 203,000 gallons
(b) Recirculation rate : 30,000 gallons/hr
(c) Cooling Towers : 3, forced draught
(d) Temperature drop : 6° C.
(e) Concentration factor : 1.5

The cooling system was in continuous use and immediately prior to the trial the level of planktonic bacteria in the system was $2 \times 10^4$/ml. Bacterial slime was present in the system pipework and on corrosion coupons placed in the system.

Four, weekly, shot doses of THPS-75 (i.e. no surfactant) to give a level of 50 ppm in the recirculating water, were carried out and although the level of planktonic bacteria and algae in the system water were substantially reduced immediately after each shot dose, the bacterial slime was not removed.

Pant Trial 3

This plant was also an open evaporative cooling system and its parameters were as follows:

(a) System Capacity : 10,500 gallons
(b) Recirculation rate : 1000 gallons/hr
(c) Cooling Towers : 1 induced draught
(d) Temperature drop : 9° C.
(e) Concentration factor : 1.5

The cooling system was in continuous use and immediately prior to the trial the level of planktonic bacteria was $10^4$/ml. The distribution channels in the cooling towers were heavily fouled with up to 4 inches depth of a green mixed algal and bacterial slime, leading to a significant reduction in tower efficiency.

One shot dose of formulation 1 (see Example 1) was added to give 50 ppm in the system water. One hour after the addition, the level of planktonic bacteria in the system water was down to zero and the slime had started to break up. A week later, half of the slime had been removed and a further 50 ppm shot dose of formulation 1 was added. After a further week it was observed that only about 10% of the original slime remained in the distribution channels and this had changed colour from green to brown indicating that the algal component was now dead. Because of the improved distribution of water in the tower, the tower efficiency had been markedly improved.

This result, when compared with plant trial 2, demonstrates the improvement in effectiveness associated with using a surfactant in combination with THPS-75.

EXAMPLE 4

Plant Trials 4 and 5

Two plant treatment programmes were carried out on a cooling water system known to be infected with legionella bacteria. In this case, treatment with THPS-75 alone failed to eliminate the bacteria whereas when used in conjuction with a nonionic surfactant, elimination was achieved.

The plant parameters were as follows:

(a) System capacity : 51,000 gallons
(b) Recirculation rate : 100,000 gallons/hr
(c) Cooling towers : 3, forced draught
(d) Temperature drop : 5° C.
(e) Concentration factor : 2.0

Parts of the plant were known to be fouled with inorganic sludge and bacterial slime and this was harbouring a variety of bacteria. In particular, the system was infected with *Legionella Pneumophila* and this was causing concern to the operators. The initial Legionella level measured was 300 bacteria per liter and the system was then treated, consecutively, with two proprietary biocides, based respectively on isothiazolone and on a mixture of an organo tin biocide and quaternary ammonium surfactant, at shot dose levels in the region of 500 ppm. Subsequent to this treatment, it was found that the level of Legionella in the system had risen to 3000 bacteria per liter.

Plant Trial 4

When the system is treated with a single shot dose of THPS-75 to give a peak level of 500 ppm in the system water the level of Legionella bacteria falls to about 2,500 bacteria per liter i.e. the treatment arrests the growth but fails to eliminate the bacteria.

Plant Trial 5

The same system was then treated with one shot dose each of THPS-75 and "EMPILAN"® KCMP 0703/F to give peak levels of 400 ppm and 20 ppm respectively in the system water. This resulted in the complete elimination of Legionella bacteria from the system.

Note

"EMPILAN" is a Registered Trade Mark of Albright & Wilson Limited; KCMP 0703/F is a nonionic surfactant. It is a mixed ehtylene oxide/propylene oxide condensate with a fatty alcohol.

EXAMPLES 5 TO 10

Mixed population biofilms were built up by exposing 1 cm diameter mild steel studs to a circulating, bacterially contaminated cooling water (see Table 1). Over a period of three weeks, a stable biofilm was built-up on the studs and they were then extracted for use in biocide tests.

The biofilm coated studs were suspended in beakers and a solution of the appropriate biocide system, made up in cooling water (Table 1), was added to each beaker. The water in each beaker was stirred with a magnetic follower and left in contact with the studs at 25° C. for 6 hours. At the end of this period, tests were performed to measure the live bacterial levels on each stud.

TABLE 1

| Cooling Water Analysis | |
|---|---|
| 1. pH Value | 8.8 |
| 2. Total Dissolved Solids | 650 ppm $CaCO_3$ |
| 3. 'P' akalinity | 70 ppm $CaCO_3$ |
| 4. 'M' Alkalinity | 450 ppm $CaCO_3$ |
| 5. Calcium Hardness | 280 ppm $CaCO_3$ |
| 6. Total Hardness | 510 ppm $CaCO_3$ |
| 7. Chloride | 50 ppm |

Example 5 to 10 are listed in Table 2:

TABLE 2

| EXAMPLE | BIOCIDE SYSTEM | CONCENTRATION | CHEMICAL TYPE OF SURFACTANT |
|---|---|---|---|
| 5 | THPS-75 | 200 | Fatty alcohol condensed with |
|   | "EMPIGEN" ® KCMP 0703/F | 20 | 10 moles ethylene/propylene oxides |
| 6 | THPS-75 | 200 | Alkylbenzyldimethylammonium |
|   | "EMPIGEN" ® BAC | 20 | Chloride |
| 7 | THPS-75 | 200 | Docecylbenzene Sodium |
|   | "NANSA" ® HS 80 | 20 | Sulphonate |
| 8 | THPS-75 | 200 | Alkyl Dimethyl Betaine |
|   | "EMPIGEN" ® BB | 20 | |
| 9 | THPS-75 | 200 | Potassium Perfluoroalkyl |
|   | "FLUORAD" ® FC 95 | 20 | Sulphonate |
| 10 | THSP-75 | 200 | Alkyl Dimethyl Amine Oxide |
|   | "EMPIGEN" ® OB | 20 | |

EMPILAN, EMPIGEN, NANSA and FLUORAD are Registered Trade Marks.

In each case the mixture of the invention substantially reduces or eliminates the bacteria compared with THPS alone.

The majority of the surfactants which are mentioned hereinbefore for use according to the invention have little or no inherent biocidal activity. Certain surfactants, such as the quaternary amines, are known to be biocidally active. In such cases we have shown that the biocidal activity of the surfactant alone is substantially less than that of THP salts at the same dosage levels. Our examples thus demonstrate an important and striking synergism between the organophosphine compounds and the surfactant.

NOTE all references herein and in the claims to adding a mixture to a water system or an aqueous based composition are to be construed as including both the addition of the preformed mixture, and the addition of the separate or partially premixed components thereof to form the mixture in situ in said water system or aqueous based composition, and also addition of the mixture or its components to a concentrate or anhydrous product which is subsequently diluted to form said system or composition.

We claim:

1. A biocidally active composition for use in water treatment consisting essentially of a synergistic mixture of:
   (A) a water soluble tetrakis (hydroxymethyl) phosphonium salt and;
   (B) at least one surfactant selected from the group consisting of anionic, nonionic and amphoteric surfactants, which are effective to lower surface tension between water and hydrophobic solid surface,
   in a proportion of A:B of from 1:50 to 1,000:1.

2. The composition according to claim 1 wherein the proportion of A:B is from 1:20 to 100:1.

3. The composition according to claim 2 wherein the proportion of A:B is from 1:1 to 20:1.

4. The composition according to claim 1 wherein the tetrakis (hydroxymethyl) phosphonium salt is the chloride, sulphate or phosphate.

5. The composition according to claim 1 wherein the surfactant B comprises an ethoxylated alcohol.

6. A composition according to claim 1 wherein the surfactant comprises $C_8$–$C_{22}$ alkyl, $C_8$–$C_{22}$ alkenyl or $C_8$–$C_{22}$ alkaryl group.

7. A composition according to claim 6, wherein the surfactant is a sulphonic or mono-esterified sulfuric acid.

8. The composition according to claim 7, wherein the surfactant is selected from the group consisting of alkylbenzene sulphonate, alkyl sulphate, alkyl ether sulphate, olefin sulphonate, alkane sulphonate, alkylphenol sulphate, alkylphenol ether sulphate, alkylethanolamide sulphate, alkylethanol amide ether sulphate and alpha sulpho fatty acid or its esters.

9. A biocidally active composition for use in water treatment consisting essentially of a synergistic mixture of:
   (A) a water soluble tetrakis (hydroxymethyl) phosphonium salt and;
   (B) at least one surfactant in a proportion of A:B of from 1:50 to 1,000:1; and wherein said surfactant is selected from the group consisting of:

an alkyl benzene sulphonate;

an alkyl dimethyl betaine;

an alkyl dimethyl amine oxide; and a potassium perfluoralkyl sulphonate.

10. A composition according to claim 9 wherein B is alkyl benzene sulphonate.

11. The composition according to claim 9 wherein the surfactant B comprises an alkyl benzene sulphonate.

12. The composition according to claim 9 wherein the surfactant B comprises an alkyl dimethyl betaine.

13. The composition according to claim 9 wherein the surfactant B comprises an alkyl dimethyl amine oxide.

14. The composition according to claim 9 wherein the surfactant B comprises a potassium perfluoralkyl sulphonate.

15. A method for the treatment of water systems which are susceptible to microbiological contamination, comprising adding thereto a biocidally active amount of the composition of claim 9.

16. A method for the treatment of water systems which are susceptible to microbiological contamination, consisting in adding thereto a biocidally active amount of a synergistic mixture of:

(A) a water soluble tetrakis (hydroxymethyl) phosphonium salt and;

(B) at least one surfactant in a proportion of A:B of from 1:50 to 1,000:1.

17. A method according to claim 16 for treating industrial cooling or process water.

18. The method according to claim 16, wherein the weight ratio of A:B is from 1:20 to 100:1.

19. The method according to claim 16, wherein the weight ratio of A:B is from 1:1 to 20:1.

20. The method according to claim 16, wherein B comprises an alkyl benzyl dimethyl ammonium chloride or an ethoxylated alcohol and the tetrakis (hydroxymethyl) phosphonium salt is the chloride, sulphate or phosphate.

21. A method for the treatment of a microbiologically contaminated water system which comprises adding thereto a synergistic mixture of:

(A) a water soluble tetrakis (hydroxymethyl) phosphonium salt and;

(B) at least one surfactant in a weight ratio of A:B of from 1:50 to 1000:1.

22. A method according to claim 21 wherein said water system is contaminated with bacterial slime.

23. The method according to claim 21, wherein the weight ratio of A:B is from 1:20 to 100:1.

24. The method according to claim 21, wherein the weight ratio of A:B is from 1:1 to 20:1.

25. The method according to claim 21, wherein B comprises an alkylbenzene sulphonate an alkyl benzyl dimethyl ammonium chloride or an ethoxylated alcohol and the tetrakis (hydroxymethyl) phosphonium salt is the chloride, sulphate or phosphate.

* * * * *